United States Patent [19]

Seelin et al.

[11] Patent Number: 5,713,666
[45] Date of Patent: Feb. 3, 1998

[54] THERMAL TESTING APPARATUS AND METHOD

[75] Inventors: Kusuma S. Seelin; Srikanth N. Seelin, both of San Jose, Calif.

[73] Assignee: Seelink Technology, San Jose, Calif.

[21] Appl. No.: 521,332

[22] Filed: Aug. 30, 1995

[51] Int. Cl.$^6$ .................................. G01J 5/00; G01J 5/54
[52] U.S. Cl. .............................................. 374/126; 374/121
[58] Field of Search ..................................... 374/120, 121, 374/126; 250/252.1 A

[56] References Cited

U.S. PATENT DOCUMENTS

| | | |
|---|---|---|
| 3,502,874 | 3/1970 | Astheimer . |
| 3,566,122 | 2/1971 | Paine . |
| 4,636,092 | 1/1987 | Hegyi . |
| 4,652,144 | 3/1987 | Günther et al. . |
| 5,094,544 | 3/1992 | Ingatowicz .................... 374/126 |
| 5,154,514 | 10/1992 | Gambino et al. . |
| 5,561,290 | 10/1996 | Strobel et al. .............. 250/252.1 A |

OTHER PUBLICATIONS

Lazzaro, G., et al., "Thermal Modeling Eases ASIC Packaging Issues" *Packaging*, pp. 56–58, Oct. 1994.
"Device Thermal Resistance Measurement by IR Scanning" *MSC*, Jan. 1977, pp. 1–6.
"Analysis Tech" brochure—Wakefield, Massachusetts.

*Primary Examiner*—Richard Chilcot
*Assistant Examiner*—Joseph L. Felber
*Attorney, Agent, or Firm*—Ashok K. Janah

[57] ABSTRACT

A method and apparatus for measuring thermal properties of electronic components (25) encapsulated in packaging is described. The method can be used to measure a junction temperature $T_j$ of the electronic component (25), without removing the package (30), and during operation of the electronic component (25) by a power supply. The method comprises the steps of (a) positioning the electronic component (25) in a field of view of an infrared sensor (90), during operation of the electronic component (25) by the power supply; (b) focusing the infrared sensor (90) on the electronic component (25) inside the package (30) to obtain (i) a sharp outline of the component, and (ii) a maximum temperature reading; (c) removing the electronic component (25) from the field of view of the infrared sensor (90); (d) positioning a blackbody source (65) capable of emitting infrared radiation at different wavelengths at substantially the same focal point as the electronic component (25); (e) calibrating the infrared sensor (90) using the blackbody source (65); (f) replacing the blackbody source (65) by the electronic component (25) while continuing to operate the electronic component (25) by the power supply; (g) adjusting the focus of the calibrated infrared sensor (90) by an amount $F_c$ sufficient to compensate for a thermal expansion movement of the electronic component (25) and package (30) caused by a rise in temperature of the electronic component (25) resulting from operation of the component by the power supply; and (h) measuring the junction temperature $T_j$ of the electronic component (25) to an accuracy of greater than 5% without removing the package (30) of the electronic component (25).

17 Claims, 7 Drawing Sheets

THERMAL TESTING APPARATUS AND METHOD

BACKGROUND

The present invention is related to thermal analysis systems and methods for measuring temperatures of packaged semiconductor devices.

Conventional semiconductor devices typically comprise an electronic component, such as an integrated circuit chip, encapsulated in an electrical insulator package, with interconnection leads extending from the package. The current trend in semiconductor device fabrication is to reduce the size of the electronic component, reduce the spacings of the metal interconnection lines in the component, and increase packing density. The higher power density of these electronic components results in an increase in operating temperature during operation of the device. Thus, fabrication of successful semiconductor devices must include consideration of the thermal properties and operational temperatures of the devices, particularly the device junction temperature $T_j$, which is the temperature of transition regions between different portions of the electronic component that have asymmetrical electrical conductivities, such as two semiconductor portions, for example p-type and n-type portions. Junction temperature is one of the primary factors affecting the reliability and performance of semiconductor devices. The importance of the junction temperature of a semiconductor device is illustrated by the rule of thumb that the lifetime of device approximately doubles for each reduction of 10° C. in junction temperature. Junction temperatures above 160° C. will almost always result in early failure of the semiconductor device. Thus, accurate determination of this junction temperature is of fundamental importance in both device and system design.

Conventional methods of measuring the junction temperature suffer from several disadvantages. For example, junction temperatures can be estimated by thermal modeling of the device to determine a theoretical temperature distribution of the device. However, thermal modeling techniques are inaccurate because they are dependent upon factors and assumptions with regard to the thermal properties of the device, package, external environment, as well as specific thermal operating conditions.

Instead of modeling the temperature distribution of a semiconductor device, the actual temperatures of the device can be experimentally determined. One method of measuring the junction temperature, know as the diode method, utilizes the principle that there is a linear relationship between forward-biased voltage drop and junction temperature when a constant forward current is applied to the junction. For example in a transistor, the base to emitter voltage is temperature dependent, and in a diode, the forward voltage is temperature dependent. The temperature dependent characteristics of these devices may be plotted to yield a graph. The devices, known as thermal dies, are inserted within a selected package in place of the semiconductor device for which it was designed, and a test is run. By using data obtained from this test in conjunction with the previously-prepared graph, the thermal characteristics of the package can be determined under various operational conditions. However, the latter technique is primarily a correlation method, which is also subject to the inaccuracies of estimated operating conditions and other factors.

Another technique uses an infrared microscope system comprising an infrared detector to measure the temperature of the exposed active surface of the electronic component of the semiconductor device, after a portion of the package is removed. In these methods, a portion of the insulator package encapsulating the component is removed by wet chemical etching or by cutting open a hole in the top surface of the package. Thereafter, the active area of the electronic component is coated with a uniform thin layer of a high emissivity material such as black pigmented lacquer or by calibrating the active area of the electronic component for its emissivity. The infrared radiance measurement of the exposed active area is converted to a temperature using the measured emissivity. Also, it is time consuming and costly to remove the packaging from the chip. Further, removal of the package results in a different thermal environment than that obtained with the package encapsulating the component, particularly because the package is generally made of a thermally insulative material, thereby reducing the accuracy of the test technique. For these reasons, conventional infrared methods are often difficult to produce accurate and reproducible measurements of the temperature of semiconductor devices.

Another limitation of conventional thermal property testing methods occurs for modern semiconductor devices having high lead counts, such as VLSI chips (very large scale integrated circuits), hybrid circuits, and ASIC's, which can typically have lead counts in excess of 200 leads, and more typically from about 200 to about 400 leads. The large number of leads creates several problems for thermal analysis of the component. For example, it is difficult to electrically connect all leads to the external environment to operate and monitor thermal operation of the device, particularly when using the diode method. Thus, typically a smaller number of lead connections are used for thermal testing and operation of the device.

Also, conventional test boards used to mount semiconductor devices are deficient in that these boards do not accurately replicate the actual operating thermal environment of the device. Often, the boards comprise a small size or a small number of layers that provides a different thermal environment than the actual test boards.

Thus, it is desirable to have a temperature measuring apparatus and method which can accurately and reproducibly measure the temperatures of semiconductor devices without removing the package of the semiconductor device, and to accuracies of greater than 5%. It is also desirable to have an apparatus that allows quick and easy programming, fixturing, and testing of semiconductor devices having high lead counts, and which allows accurate replication of the thermal environment of the device during actual operation. It is also desirable to avoid the use of expensive test equipment, while increasing the speed, accuracy, and ease with which the thermal properties of a semiconductor device can be determined.

SUMMARY

The present invention satisfies these needs, by providing a method of measuring the thermal properties of a semiconductor device. In particular the method allows measurement of the junction temperature $T_j$ of an electronic component encapsulated in a package, without removing the package, and during operation of the electronic component by a power source, the method comprising the steps of:

(a) positioning the electronic component in a field of view of an infrared sensor, during operation of the electronic component by the power source;

(b) focusing the infrared sensor on the electronic component inside the package to obtain (i) a sharp outline of the component, and (ii) a maximum temperature reading;

(c) removing the electronic component from the field of view of the infrared sensor;

(d) positioning a blackbody source capable of emitting infrared radiation at different wavelengths at substantially the same focal point as the electronic component;

(e) calibrating the infrared sensor using the blackbody source;

(f) replacing the blackbody source by the electronic component while continuing to operate the electronic component by the power source;

(g) adjusting the focus of the calibrated infrared sensor by an amount $F_c$ sufficient to compensate for a thermal expansion movement of the electronic component and package caused by a rise in temperature of the electronic component resulting from operation of the component by the power source; and (h) measuring the junction temperature $T_j$ of the electronic component to an accuracy of greater than 5% without removing the package of the electronic component.

Another aspect of the invention provides an apparatus for measuring a junction temperature of an electronic component in a package, without removing the package, and during operation of the electronic component, the apparatus comprising:

(a) a sensor assembly having a field of view, the sensor assembly comprising an infrared sensor;

(b) an adjustable platform in the field of view of the sensor assembly;

(c) a blackbody source mounted on the platform, the blackbody source having a emitter capable of emitting infrared radiation at different temperatures $T_b$ for calibration of the infrared sensor; and (d) a holder mounted on the platform for holding the package with the electronic component therein, wherein the blackbody source and holder are mounted on the platform so that the package of the electronic component when held in the holder is substantially in the same focal plane as the emitter of the blackbody source.

A further aspect of the invention comprises a test fixturing board for holding a packaged electronic component having external leads, for measuring thermal properties of the electronic component during operation of the component. The test fixturing board comprises (a) an insulator;

(b) a top surface having first circuit grid interconnections, at least some of the interconnections capable of mating with the external leads of the packaged electronic component;

(c) a bottom surface having second circuit grid interconnections suitable for electrically connecting the board to the external environment;

(d) an electrically conductive ground layer in the insulator, the ground layer having conductive ground connectors extending therefrom, and through at least a portion of the insulator, to electrically connect the ground layer to selected grid interconnections on the top and bottom surfaces, the ground connectors proximately located at less than about 1 cm from the leads of the packaged electronic component; and (e) an electrically conductive power layer in the insulator, the power layer having conductive power connectors extending therefrom, and through at least a portion of the insulator, to electrically connect the power layer to selected grid interconnections on the top and bottom surfaces, the power connectors proximately located at less than about 1 cm from the leads of the packaged electronic component, whereby the proximately located ground and power connectors allow measurement of the thermal properties of the packaged electronic component during operation of the component with an accuracy of greater than 5%.

DRAWINGS

These and other features, aspects, and advantages of the present invention will become better understood with regard to the following description, appended claims, and accompanying drawings which provide illustrative examples of the invention, where:

DESCRIPTION

Figures 1A, 1B:
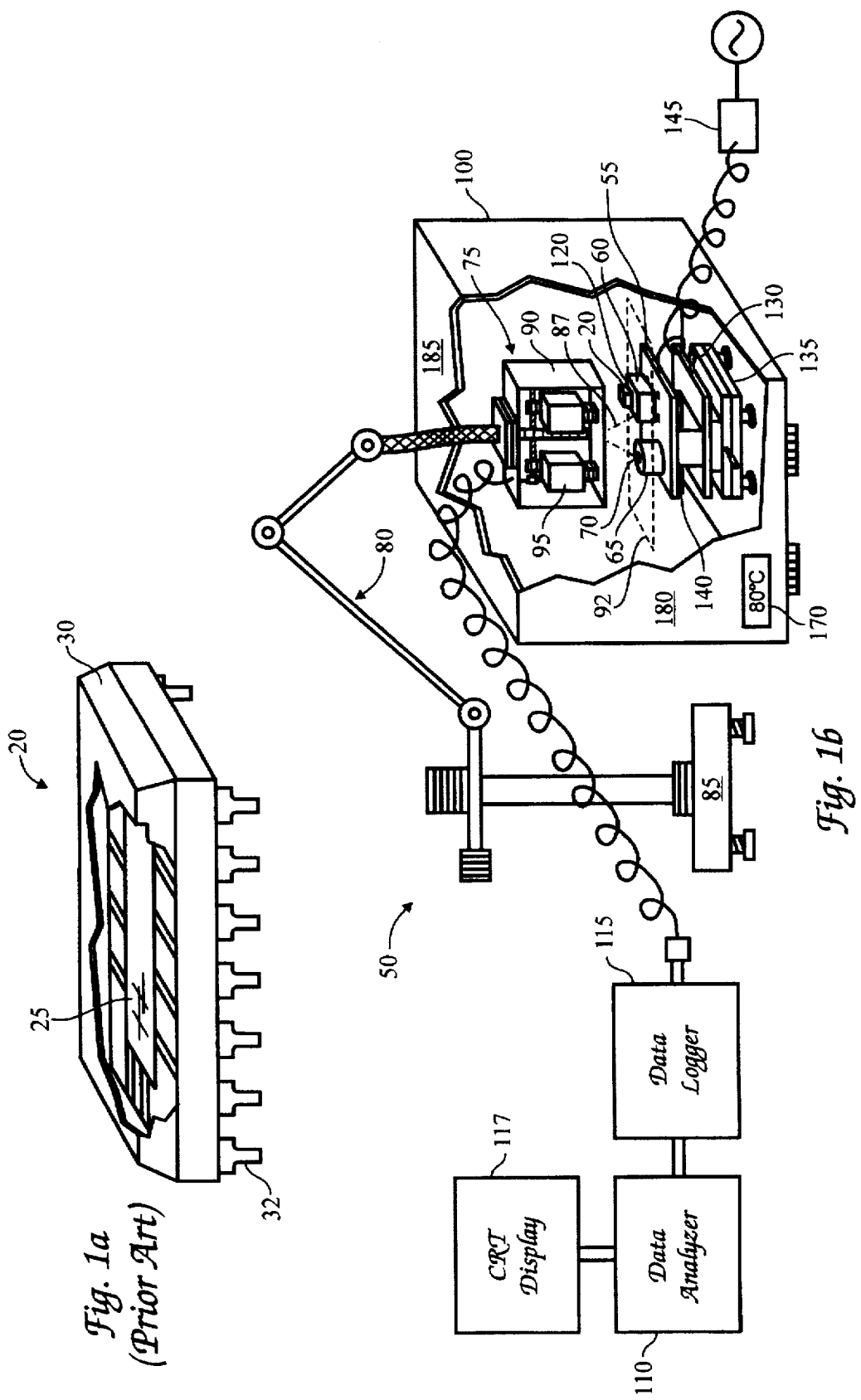
FIG. 1a (prior art) shows a partical cutaway schematic view of a typical semiconductor device, showing the electronic component in the device.
FIG. 1b shows a schematic of a thermal testing system of the present invention.

The present apparatus and method can be used to determine the thermal properties of semiconductor devices 20 comprising an electronic component 25 encapsulated in an electrically insulative package 30, with electrical connection leads 32 extending from the package, as shown in FIG. 1a, such as an integrated circuit chip, resistor, transistor, capacitor, induction coil, and switching devices. Semiconductor devices 20 are typically placed within packages 30 designed to secure and contain the devices during operation. Typical packages 30 include conventional DIP (dual-in-line) packages 30 made of plastic, hybrid units, SMT type units, flat pack units, and encapsulated multichip modules.

A key aspect of the thermal analysis system 50 and method of the present invention lies in the ability of the system to measure the temperatures of an encapsulated semiconductor device 20 without removing the packaging of the device. In many situations, removal of the packaging is difficult and undesirable because it changes the thermal environments of the integrated circuit chip within the packaging. Also, eliminating the step of removing the package from the device saves time and effort. Furthermore, the present invention measures actual temperatures of the electronic component 25, such as junction temperatures $T_j$, with an accuracy of at least about or better than 5%, and more typically with an accuracy of about 2 to 3%, while conventional methods provide an accuracy of only 10%. Most typically the junction temperature $T_j$ of the electronic component 25 is measured to an accuracy of at least about 1° C. at a temperature of about 50° C. Also, the thermal analysis technique can be used to nondestructively measure the operating temperatures of semiconductor devices 20 for quality assurance purposes, without destroying the integrity of the semiconductor device 20.

With reference to FIG. 1b, the thermal testing apparatus of the present invention generally comprises an adjustable test platform 55 comprising (i) a holder 60 for holding a semiconductor device 20 comprising a package 30 with an electronic component 25 therein, and (ii) a blackbody source 65 mounted on the platform 55, the blackbody source 65 having a emitter 70 capable of emitting infrared radiation at different temperatures $T_b$ for calibration of the infrared sensor 90. The blackbody source 65 and holder 60 are mounted on the platform 55 so that the package 30 of the electronic component 25 when held in the holder 60, is substantially in the same focal plane 92 as the emitter 70 of the blackbody source 65. A sensor assembly 75 is held by an adjustable arm 80 mounted on a stabilizing stand 85, the adjustable arm 80 allows movement of the sensor assembly 75 so that the field of view 87 of the sensor assembly encompasses either the semiconductor device 20 or the blackbody source 65. The sensor assembly 75 typically comprises an infrared sensor 90 for measuring temperatures, and optionally, an optical sensor 95 for coarse focusing of the sensor assembly 75 on the packaged semiconductor device 20. Optionally, an enclosure 100 is used to enclose the platform 55 and sensor assembly 75 to reduce adverse environmental effects on the testing system. A data analyzer system 110 is connected to the sensor assembly 75, electronic component 25, and blackbody source 65 via a data logger 115, to monitor and analyse signals from these devices, and display the results on a CRT display 117.

The platform 55 of the apparatus can be any conventional platform suitable for holding and positioning a semiconductor device 20 and blackbody source 65. Typically, the platform 55 includes (i) a holder 60 suitable for holding the semiconductor device 20, such as a plug-in module containing a plurality of holes 120 sized and configured to fit the leads 32 extending from the semiconductor device 20 so that the semiconductor device 20 rests substantially horizontally on the platform 55, and (ii) a portion on which the blackbody radiator is removably mounted. The holder 60 of the platform 55 is shaped, sized, and configured to mount various semiconductor devices 20 thereon, such as for example, a BGA (ball grid array) or a PLCC (plastic leadless chip carrier), or QFP (quad flat pack), or multi-chip module. It is a feature of the invention that the blackbody source 65 is mounted so that its emitter 70 is substantially on the same local plane 92 as the upper surface of the packaged semiconductor device 20. By focal plane 92 it is meant the same plane as that the infrared sensor 90 is focused upon. This allows positioning of the platform 55 so that the blackbody source 65 is moved horizontally into the field of view 87 of the sensor assembly 75 without removing the semiconductor device 20 from the platform 55. Optionally, the holder 60 or plug-in module is mounted on a conventional test circuit board, or a preferred test fixturing board 125 as shown in FIGS. 6–9, that is suitable for mounting the semiconductor device 20.

The platform 55 is supported by an XYZ horizontal table 130 which allows three-dimensional movement of the semiconductor device 20 and blackbody source 65, in order to focus the sensor assembly 75 on the either device. Preferably, the XYZ positioning table 130 is mounted on a vibration absorbing plate 135, a suitable vibration absorbing plate 135 commercially available from Vibraplane.

Optionally, a temperature regulator 140 can be used to regulate the temperature of the platform 55 to heat or cool the semiconductor device 20 mounted on a platform 55. The temperature regulator 140 either supplies additional heat to the platform 55 using a thermal resistor mounted adjacent to the platform 55, or cools the platform 55 using a thermoelectric module built into the platform 55. A suitable temperature regulator 140 is a manufactured by Melcor Company, New Jersey.

A powering device 145 which may be a power supply or a power system is connected to the semiconductor device 20 to operate the device. The powering system can include instrumentation or a computer system specially adapted to provide input signals to specific leads 32 of the semiconductor device 20 and to monitor output signals from other output leads 32 of the semiconductor device 20. This allows complete monitoring and operation of the semiconductor device 20 in an environment that simulates the actual environment of the semiconductor device 20. For example, if a CPU integrated circuit device 20 is being tested, the powering system would input signals corresponding to the signals received by the CPU device 20 in an actual computer system, and receive and analyze output signals from the device 20 that correspond to signals outputted by the device 20 in an actual operating computer system.

Figure 2:
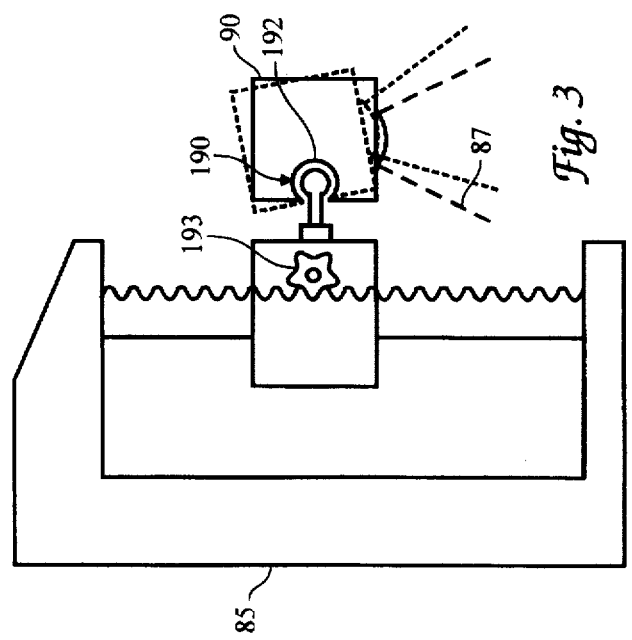
FIG. 2 shows a side schematic view of a sensor assembly of the present invention showing the infrared and optical sensors of the assembly and the gimbal mechanism.

The blackbody source 65 for mounting on the platform 55 generally comprises a radiation reflecting body 150 comprising a hollow cylinder 155 narrowing at one end to a cone, with an emitter hole 70 at the tip of the cone, as shown in FIG. 2. The cylinder 155 is coated with a blackened coating to provide a cavity which is more sensitive to all wavelengths of incoming radiation in the ultraviolet, visible, and infrared ranges. A thermal insulator 160 surrounds the body 150 except for the emitter hole 70 to maintain the cylinder at an isothermal predetermined temperature. The body 150 is suspended from the thermal insulator 160 by suitable thermal insulator 160, such as glass spacing rods. A heating and temperature sensing coil 165 is wrapped around the body. When a voltage is applied to the coil 165, the coil 165 heats up thereby emitting infrared radiation inside the body. The radiation is reflected in the body and emitted from the emitter hole 70. The magnitude of the voltage applied to the coil 165 is a measure of radiation emitted by the emitter 70. Preferably the blackbody source 65 has a temperature readout 170 which shows the temperature of the radiation emitted by the emitter 70 of the blackbody source 65. A suitable blackbody source 65 is described in U.S. Pat. No. 3,566,122, to Paine and Kendall.

The sensor assembly 75 comprises an infrared sensor 90 and an optical sensor 95, the sensors aligned relative to one another so that both have a field of view 87 that encompasses a single object. Any conventional infrared sensor 90 can be used, suitable infrared sensors 90 including indium and antimonide sensors, such as those manufactured by Barnes Engineering Company, Stamford, Conn. The infrared sensor 90 comprises a housing enclosing a fixed focal length objective lens mounted in front of a infrared detector. Preferably, the half power diameter of the objective lens of the infrared sensor 90 is at least about 5 times the minimum width of length of the area of measurement of the semiconductor device 20, such as a junction temperature area. A suitable infrared sensor 90 is capable of measuring radiation in the 1 to 6 micrometer range and has the ability to detect radiation emitted from an area having a spacial resolution of less than 40 micrometers diameter and a temperature resolution of 0.5° C. to 60° C. A suitable infrared sensor 90 is described in U.S. Pat. No. 3,502,874, to Astheimer, which is incorporated herein by reference. The sensor comprises an objective lens which focuses incoming infrared energy from a field of view 87 onto an immersed thermistor detector, after the energy is reflected from a plane scanning mirror. Typically, the field of view 87 of the sensor is 0.25 to 1.0 inch or higher, and a spatial resolution of at least about 0.006 to 0.024.

The optional optical sensor 95 of the sensor assembly 75 is any conventional adjustable focal length optical sensor 95 which includes lenses, filters, and a focus adjusting mechanism suitable for focusing the sensor on the semiconductor device 20. The sensor can include a shutter to limit the size of the field of view 87 of the optical sensor 95 to obtain the desired image. Thus, for example, to measure a junction temperature of a semiconductor device 20, a lens having a close up focus is used, whereas to measure the temperature distribution of an entire PC board, a lens having a large field of view is selected. Preferred optical sensors 95 are manufactured by Bruel and Kajaer Company.

Preferably, an enclosure 100 is formed around the sensor assembly 75 and platform 55 so that external light does not enter the sensor assembly 75 to provide more accurate infrared readings. A suitable structure comprises a front door 180 and a top door 185. When the front door 180 is lowered, this allows access for mounting and positioning the semiconductor device 20 on the platform 55. After mounting the semiconductor device 20, the front door 180 is closed, and the top door 185 is opened to allow movement of the sensor assembly 75 to allow positioning of the sensor assembly 75 above the semiconductor device 20. Once the sensor assembly 75 is accurately positioned, the top door 195 is closed, and thereafter thermal measurements are made.

Typically, the sensor assembly 75 is supported by a conventional adjustable arm 80 suitable for holding and positioning the sensor assembly 75 above the platform 55. The adjustable arm 80 is attached to a stabilizing stand 85 having a stable construction to prevent movement and misalignment of the sensor assembly during operation of the apparatus. The adjustable arm 80 can also comprise robotic systems (not shown) such as those which are known to those of ordinary skill in the art to move and position the sensor assembly 75 above the semiconductor device 20 without operator assistance.

Figure 3:
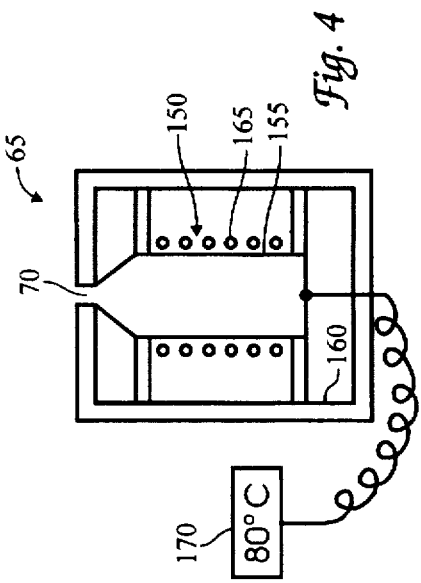
FIG. 3 shows a side view of the sensor assembly of FIG. 2 showing the gimbal mechanism.
Figure 4:
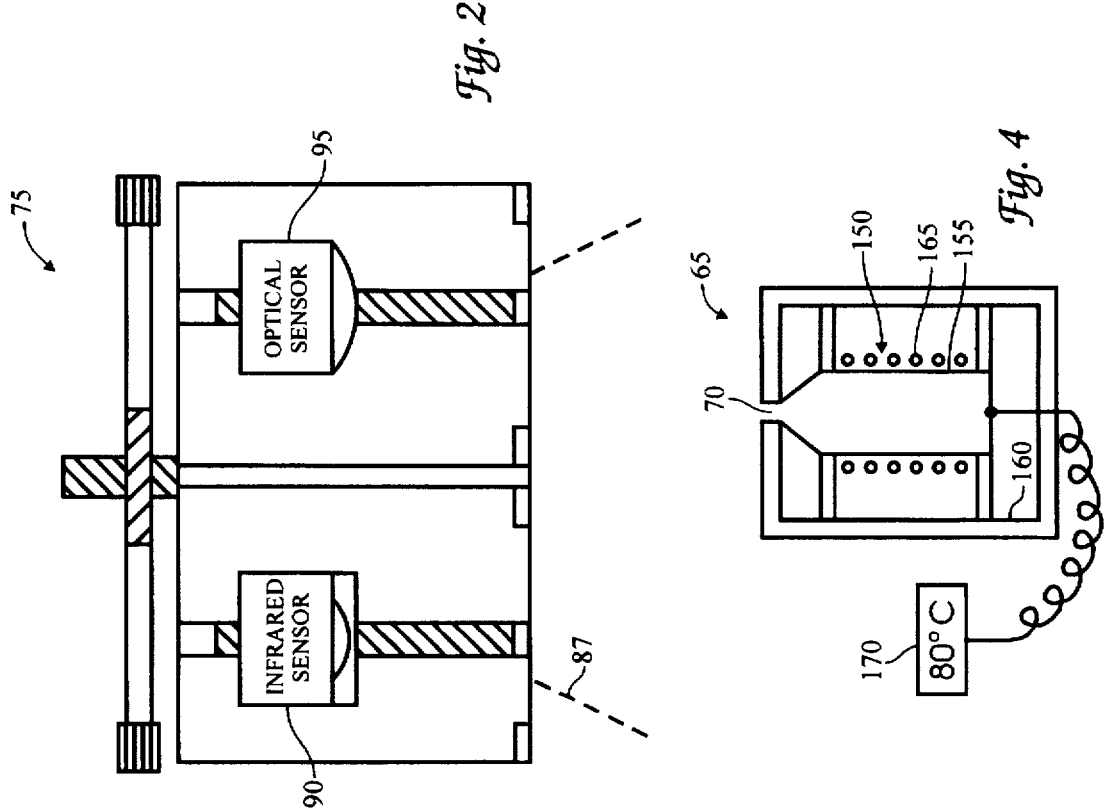
FIG. 4 shows a side crossectional schematic view of a blackbody source.

In another aspect of the invention, an adjustable gimbal system 190 is used to mount the sensor assembly 75 to the adjustable arm 80. The gimbal system 190 allows rotational adjustment of the sensor assembly 75 in a fixed plane perpendicular to the plane of the packaged semiconductor device 20. The gimbal system 190 allows adjusting the focus of the infrared sensor 90 by an amount $F_c$ sufficient to compensate for thermal expansion movement of the electronic component 25 and package 30 caused by a rise in temperature of the electronic component 25 resulting from operation of the component. A typical gimbal system 190 comprises a round gimbal ball and socket 192, the socket end attached to the infrared sensor 90 (and optionally the optical sensor 95), and the fixed round end attached to a rack and pinion system 193. The rack and pinion system 193 allows upward and downward movement of the sensors, while the gimbal mechanism 190 allows rotation of the sensor 90 a fixed plane perpendicular to the plane of the packaged semiconductor device 20 so that the field of view 87 and focus of the infrared sensor change as shown by the dotted lines of FIG. 3.

A data logger 115 is used to log data from the semiconductor device 20, infrared sensor 90, and blackbody source 65. The data logger 115 is electrically connected to each of these devices and logs the data output of the devices. A preferred data logger 115 commercially available from Matlab Company, generally comprises (i) a math co-processor function board, (ii) a graphics analyzer function board, and (iii) an analog to digital converter function. The data logger 115 can comprise additional functions as would be obvious to one of ordinary skill in the art of data logging activities.

The output data from the data logger 115 is connected to a data analyzer 110 suitable for analyzing the output data. Preferred data analyzer 110 boards include statistical data analyzer 110 boards, such as the MATLAB board. Alternatively, the data analyzer 110 board can be connected to a computer data analysis module including a software program capable of analyzing the data emitted by the data logger 115 or the statistical data analyzer 110. The software program in the computer system can also receive input signals from the infrared sensor 90 to determine a calibration curve for the infrared sensor 90. Conventional computer software programs for data analysis can be used to analyze the data to determine one or more of the following thermal properties of semiconductor devices 20, including junction temperature; thermal resistance of the device 20 in reference to package 30, mounting board temperatures or ambient temperatures; and thermal response time, as described below.

Another aspect of the invention provides a test fixturing board 125 useful for holding a packaged electronic component 25 having external leads 32, for measuring thermal properties of the electronic component 25 during operation of the semiconductor device 20. The test fixturing board 125 can be sized and configured to allow the test fixturing board 125 to be mounted on the platform 55 of the thermal test apparatus, or sized and configured for use by itself without an associated thermal test apparatus. Thus, although use of the test fixturing board 125 is illustrated by example of a thermal test apparatus, the test fixturing board 125 can also be used independently, or for other types of testing, such as for quality assurance purposes or to ensure that the electronic components 25 of the semiconductor device 20 operate properly. Typically, the test fixturing board is rectangular in shape, and sized about 6×4.5 inches, to correspond to the shape and size of typical printed circuit boards.

Generally, the test fixturing board 125 comprises multiple electrically conductive layers embedded in an electrical insulator 200. Any conventional electrical insulator that is sufficiently rigid to form a supporting board structure can be used as the insulator of the fixturing board 125. Suitable polymeric insulators include polyimide, polyketone, polyetherketone, polysulfone, polycarbonate, polystyrene, nylon, polyvinylchloride, polypropylene, polyethersulfone, polyethylene terephthalate, fluoroethylene propylene copolymers, cellulose, triacetates, silicone, and rubber. A suitable insulator 200 for the test circuit board comprises FR-4 commercially available from Dupont de Nemours Chemical Company. The insulator 200 typically has a resistivity of about $10^{15}$ Ω/cm, and a dielectric constant of at least about 3. For an insulator 200 having a dielectric constant of about 3.5, each layer of the insulator separating the electrically conductive layers from one another is typically about 100 µm thick, and more typically from about 100 to about 500 µm thick.

Figure 6:
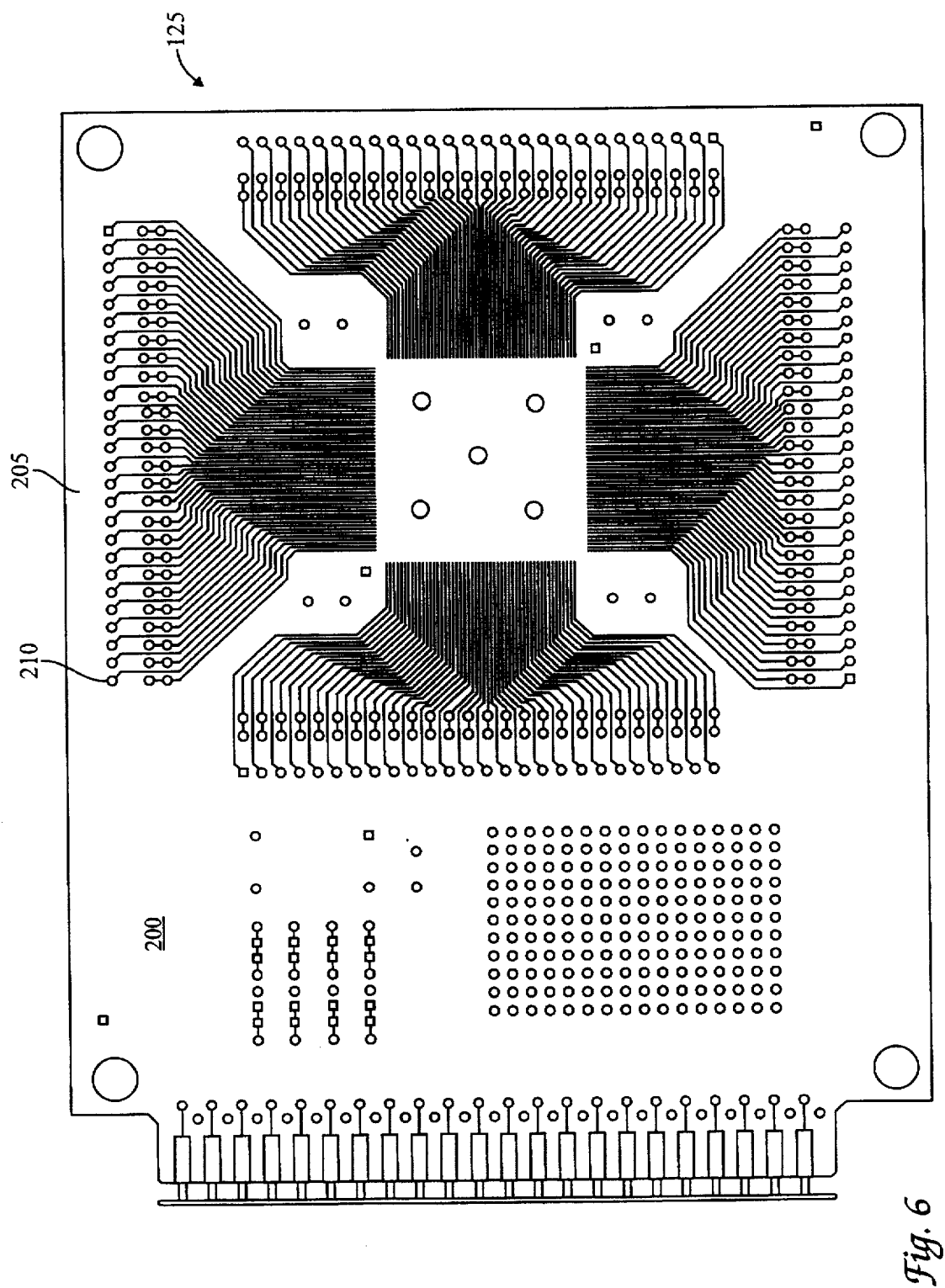
FIG. 6 shows a top view of the top surface of the test fixturing board of the present invention.

The fixturing board 125 has a top surface 205 having first electrical conductive circuit grid interconnections 210; at least some of the interconnections capable of mating with the external leads 32 of the packaged electronic component 25, as shown in FIG. 6. The grid interconnections 210 are typically made from an electrically conductive material, such as for example, metals including copper, nickel, chromium, aluminum, iron, and alloys thereof. Typically, the thickness of the grid interconnection lines are from about 0.5 µm to 100 µm, and more typically from about 1 µm to 50 µm. A suitable top surface circuit grid interconnection lines can be made by etching a ½-ounce grade copper sheet. Alternativley, the grid interconnections can be made by (i) coating an electroplating resistant resist material in the negative grid of the desired interconnection pattern on a shhet of insulator 200 as generally described in *Silicon Processing for the VLSI Era, Volume 1: Process Technology*, by Stanley Wolf and Richard N. Tauber, Lattice Press, California (1986); U.S. Pat. No. 4,952,528, to Abe, et al; U.S. Pat. No. 5,079,600, to Schnur, et al; U.S. Pat. No. 5,221,422, to Das, et al; all of which are incorporated herein by this reference, and (ii) using conventional copper electroplating methods to plate the circuit grid interconnections 210 on the exposed insulator 200 portions, using conventional copper plating techniques such as those disclosed in U.S. Pat. No. 5,252,196, to Sonnenberg, et al.; U.S. Pat. No. 5,004,525, to Bernards, et al.; U.S. Pat. No. 4,898,647, to Luce, et al.; and U.S. Pat. No. 4,948,474, to Miljkovic, which are incorporated herein by reference. Residual resist is then removed using a conventional acid stripping processes.

The top surface 205 can also have a plug-in module (not shown) mounted on the top surface 205 for removably electrically connecting the leads 32 of the packaged electronic component 25 to the grid interconnections 210 on the top surface 205, during testing of the semiconductor device 20. The design of the grid interconnections 210 on the top surface 205 of the fixturing board 125 depend on the type of semiconductor device and package design intended to be mounted on the fixturing board 125. The grid interconnections 210 can be designed to mount a wide range of semiconductor device 20 package 30 styles, including for example, standard DIP and SIP packages, surface modified devices, and pin grid arrays having 10 microinch leads pitch on 0.3, 0.4, 0.6, and 0.9 microinch row spacings. The fixturing board 125 is particularly useful for holding and electrically connecting semiconductor devices 20 that have a large number of leads 32 extending from the package 30, the number of leads typically being about at least about 200, and more typically from about 200 to about 500 leads.

Figure 7:
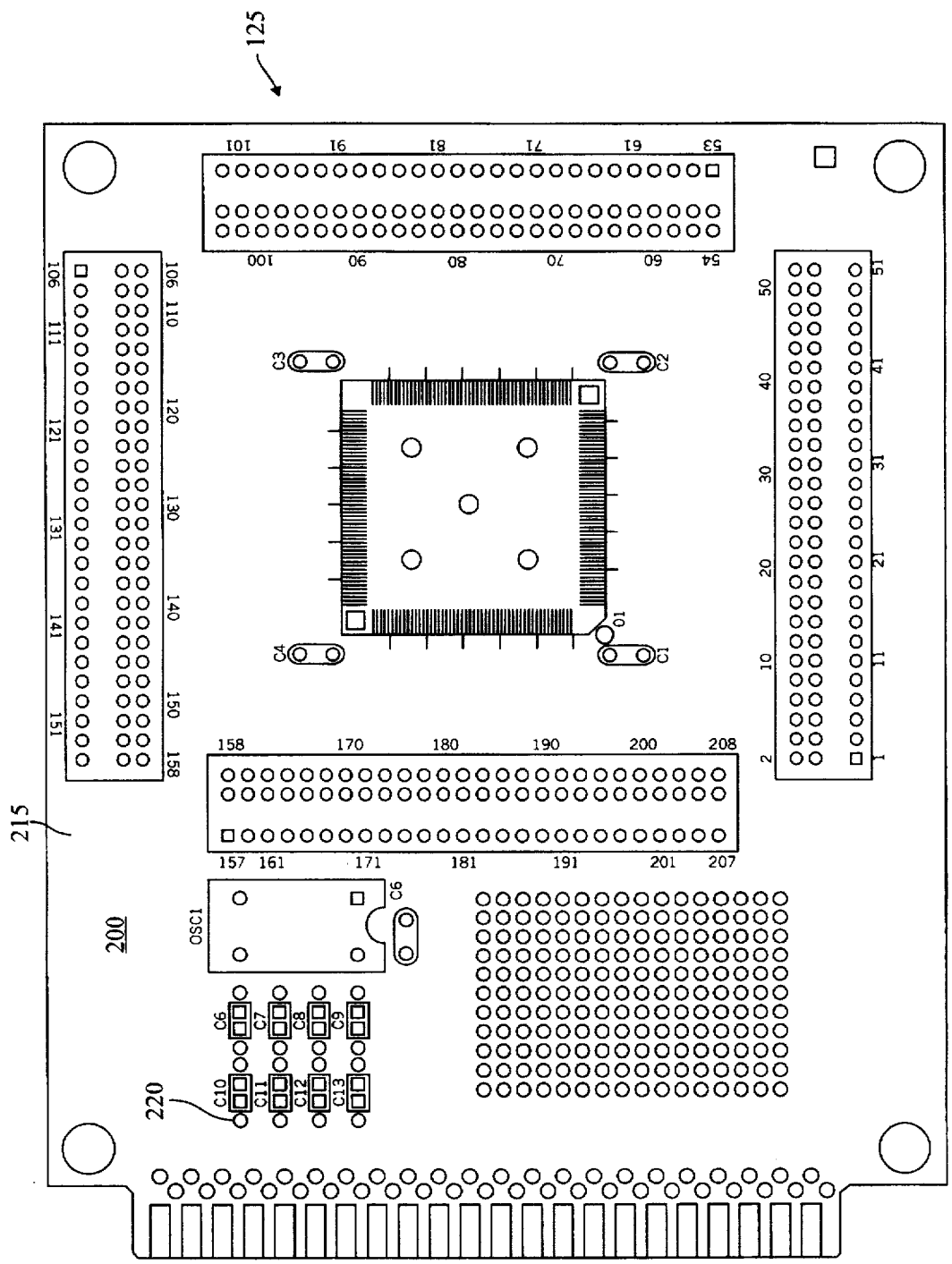
FIG. 7 shows a top view of the bottom surface of the test fixturing board of FIG. 6.

The test fixturing board 125 further comprises a bottom surface 215, as shown in FIG. 7, having second electrically conductive circuit grid interconnections 220 suitable for electrically connecting the board to the external environment. A suitable bottom surface layer 215 can be made in the same manner as the top surface layer 205. During the thermal testing of the semiconductor device 20 mounted on the board, particular grid interconnections 220 on the bottom surface 215 of the test fixturing board 125 which extend through the board to connect to the device 20 mounted on the top surface 205 of the board, are connected via soldered wires to the thermal test apparatus 50 and to the power supply 145 used to operate the device 20.

Figure 8:
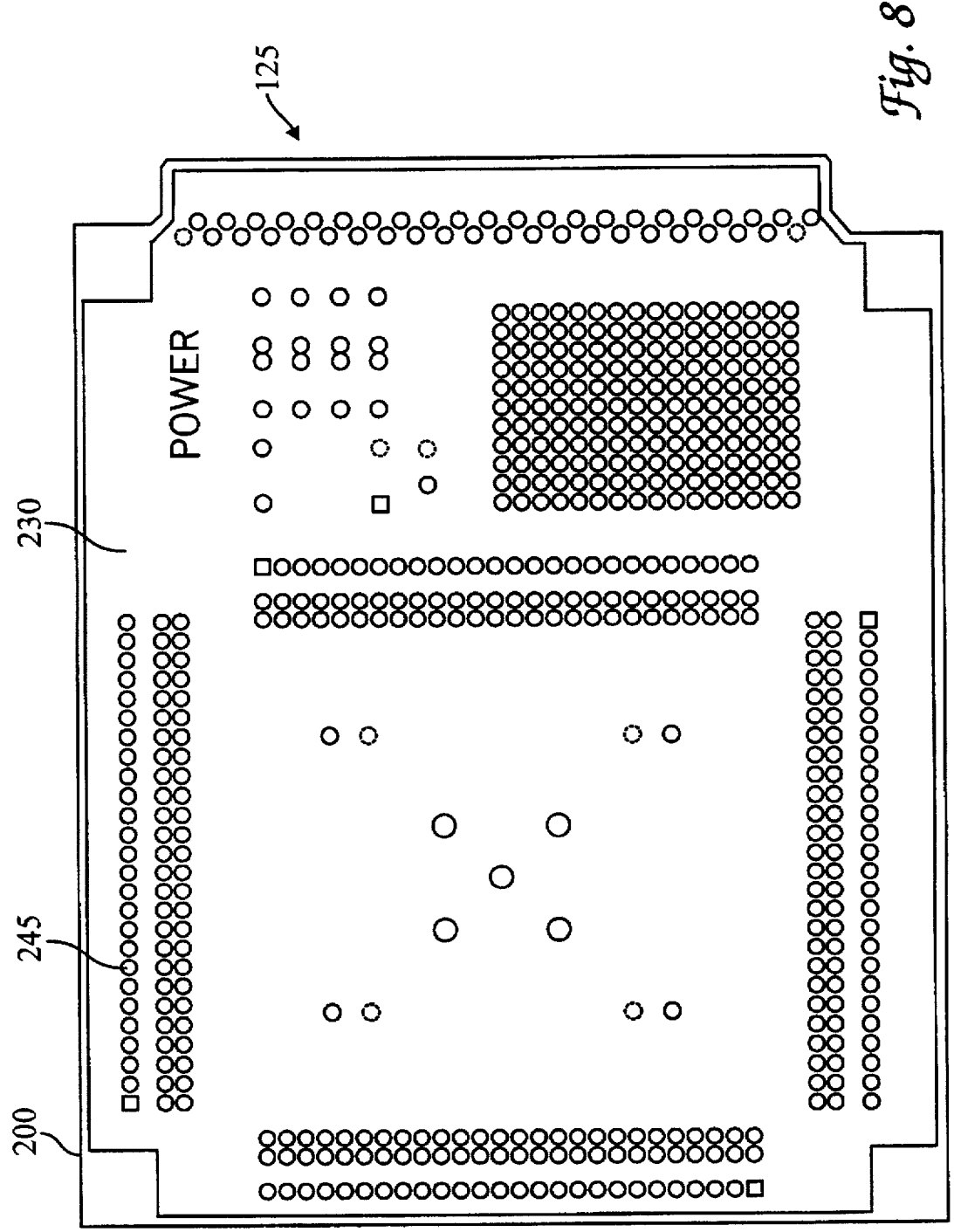
FIG. 8 shows a top view of the power plane of the test fixturing board of FIG. 6.
Figure 9:
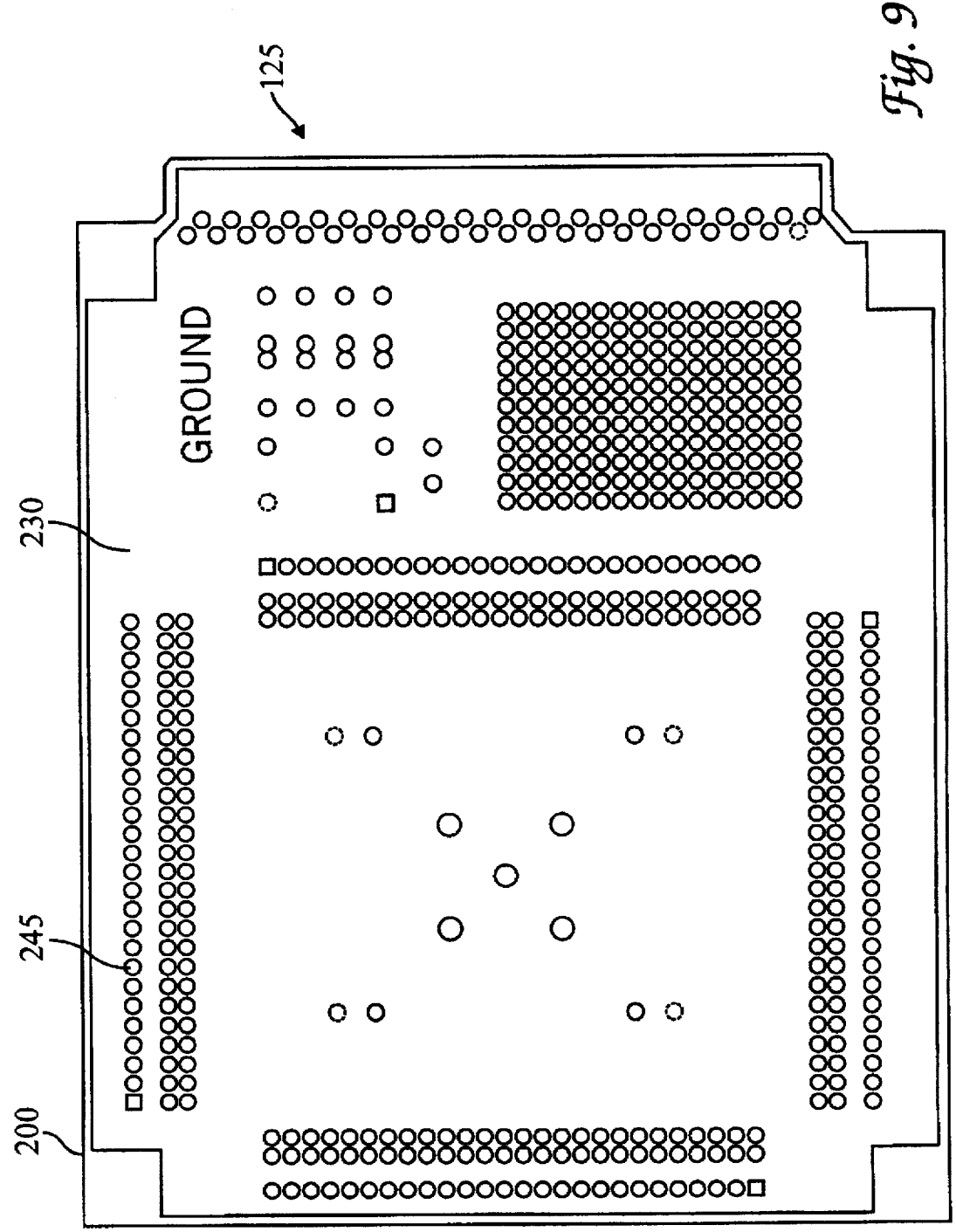
FIG. 9 shows a top view of the ground plane of the test fixturing board of FIG. 6.

The test fixturing board 125 also comprises (i) an electrically conductive ground layer 230 as shown in FIG. 8; and (ii) an electrically conductive power layer 235, as shown in FIG. 9. The top surface, bottom surface, ground and power layers are separated from each other by the insulator 200. The ground and power layers are typically made from a 1-ounce grade copper sheet; however, the power layer 235 can be made from a 2-ounce copper sheet for higher power level devices. The ground layer 230 has electrically conductive ground connectors 240 extending from the ground layer 230 through at least a portion of the insulator 200 to electrically connect the ground layer 230 to selected grid interconnections 210, 220 on the top and bottom surfaces 205, 215 of the board. Similarly, the power layer 235 also has conductive power connectors 245 extending through at least a portion of the insulator 200, to electrically connect the power layer 235 to selected grid interconnections 210, 220 on the top and bottom surface 205, 215. The ground and power layers 230, 235 and the ground and power layer connectors 240, 245 are formed by electroplating and resist techniques as described above. It has been discovered that proximately locating the ground and power connectors at less than about 1 cm from the leads 32 of the packaged electronic component 25 so that the leads 32 can be electrically connected to the external power supply and thermal test apparatus with minimized length of wiring, significantly improve the accuracy of the thermal tests performed on the packaged semiconductor device 20. In tests conducted using the test fixturing board 125, the proximately located ground and power connection connectors allowed measurement of the thermal properties of a packaged semiconductor device 20 during operation of the device to accuracies of greater than 5%, and more typically greater than about 2%, without removing the package of the device 20. It is believed that the significantly improved temperature measurements occur because of the reduced line impedance of the electrical wiring used to connect the semiconductor device 20 to the external environment. Also, excessive lengths of wire leads 32 function as heat sinks which further reduce the accuracy of the test method.

Preferably, the test fixturing board 125 is designed to provide a thermal environment, and in particular a heat dissipation environment similar to the actual environment seen by the semiconductor device 20 during operation of the device. Thus, 4-layer boards are preferred for testing computer CPU devices 20 because they more closely replicate the actual computer motherboard. Also, the grid interconnections on the board 125 are patterned to be similar to those of the printed circuit board the device 20 will actually be mounted during operation of the device 20 to further match the heat dissipating environment of the device. The test fixturing board 125 can further comprise inner thermal layers of thermally conductive or insulative materials that are used in the actual operating environment of the semiconductor device 20 and which affect the thermal environment of the device 20.

To use the test fixturing board 125, the semiconductor device 20 is soldered in the plug-in module on the top surface 205 of the board. The semiconductor device 20 is "programmed" by determining the particular lead connections required to be connected to the thermal analysis apparatus, ground plane, power plane, and optionally to a clock drive of the computer data analysis system. The test fixturing board 125 provides the ability to quickly and easily surface mount a semiconductor device 20 and try various connection and power schemes using jumper wiring until the desired connection and configuration for the leads 32 is achieved. Generally, the larger the number of leads 32 of the semiconductor device 20, the more difficult is the programming task. The test fixturing board 125 has the advantage of quick and convenient testing of modern semiconductor devices 20 having high device density and more than 200 leads.

The test fixturing board 125 is also designed to facilitate connection of the leads 32 of the semiconductor device 20 to (i) a power supply 145 for operating the device, and (ii) a computer data analysis and signal generator system (not shown) adapted to provide input signals to specific leads 32 of the semiconductor device 20 and to monitor output signals from other leads 32 of the semiconductor device 20, allowing complete monitoring and operation of the semiconductor device 20 in an environment that simulates the actual environment of the semiconductor device 20. The computer system can also be configured to continuously monitor the temperature of single or multiple different portions of the semiconductor device 20 so that the measured temperatures can be correlated to the operating environment of the semiconductor device 20 over time to obtain thermal graphs of specific sites or junctions on the chip as a function of time and as a function of operational load, i.e., the number of computations carried out at a specified time by the integrated circuit chip.

With reference to FIG. 1, a method of using the thermal testing apparatus will now be described. The semiconductor device 20 is mounted on the platform 55 by soldering the device into the plug-in module on the platform 55, or by mounting the device into a test fixturing board 125 as described below. The semiconductor device 20 is then powered by connecting the appropriate leads 32 of the device to a power supply 145, to obtain operating temperatures of the semiconductor device 20. Typically, the semiconductor device 20 is powered using conventional power supply, which varies according to the size and nature of the semiconductor device 20, or by computer software providing signals to the device 20 to simulate an actual operating condition of the device 20.

The XYZ table 130 is used to position the platform 55 below the sensor assembly 75 so that the semiconductor device 20 lies within the field of view 87 of the infrared sensor 90 and optional optical sensor 95. The optical sensor 95 is focused on the package 30 of the semiconductor device 20 to obtain a visual image of the packaged electronic device. Use of the optical sensor 95 facilitates coarse focusing of the sensor assembly 75 on the packaged electronic component 25. Thereafter, the infrared sensor 90 is fine focused on the desired portion of the semiconductor device 20. To measure junction temperature, the infrared sensor 90 is scanned over the whole active area of the powered electronic component 25 and focused on the maximum radiance measurement of the electronic component 25 (that corresponds to the highest junction temperature of the component). The infrared image desired is that of the infrared radiation emitted by the electronic component 25 inside the package 30 of the semiconductor device 20. Thus, the infrared sensor 90 is focused to a location inside the semiconductor device package 30 and on the surface of the electronic component 25 therein to obtain (i) a sharp outline of the electronic component 25, and (ii) a maximum temperature reading.

Thereafter, the semiconductor device 20 is removed from the field of view 87 of the sensor assembly 75, and the emitter 70 of blackbody source 65 is positioned in the same focal point as the semiconductor device 20 by adjusting the XYZ table 130. By focal point it is meant the position in space at which the infrared sensor is focused on. This procedure allows the infrared sensor 90 of the sensor assembly 75 to read the radiation emitted by the emitter 70 of the blackbody source 65 substantially without re-adjusting the focus of the infrared sensor 90. Because the infrared sensor 90 is maintained at the same focus, the resultant calibration of the sensor 90 and the temperature measurements on the semiconductor device 20 bear a one-to-one correspondence that allows highly accurate measurement of the thermal properties and temperature measurements of the semiconductor device 20. Also, because the focus of the infrared sensor 90 is maintained without adjustment to a position inside the semiconductor device 20, more accurate temperature measurements are possible.

Figure 5:
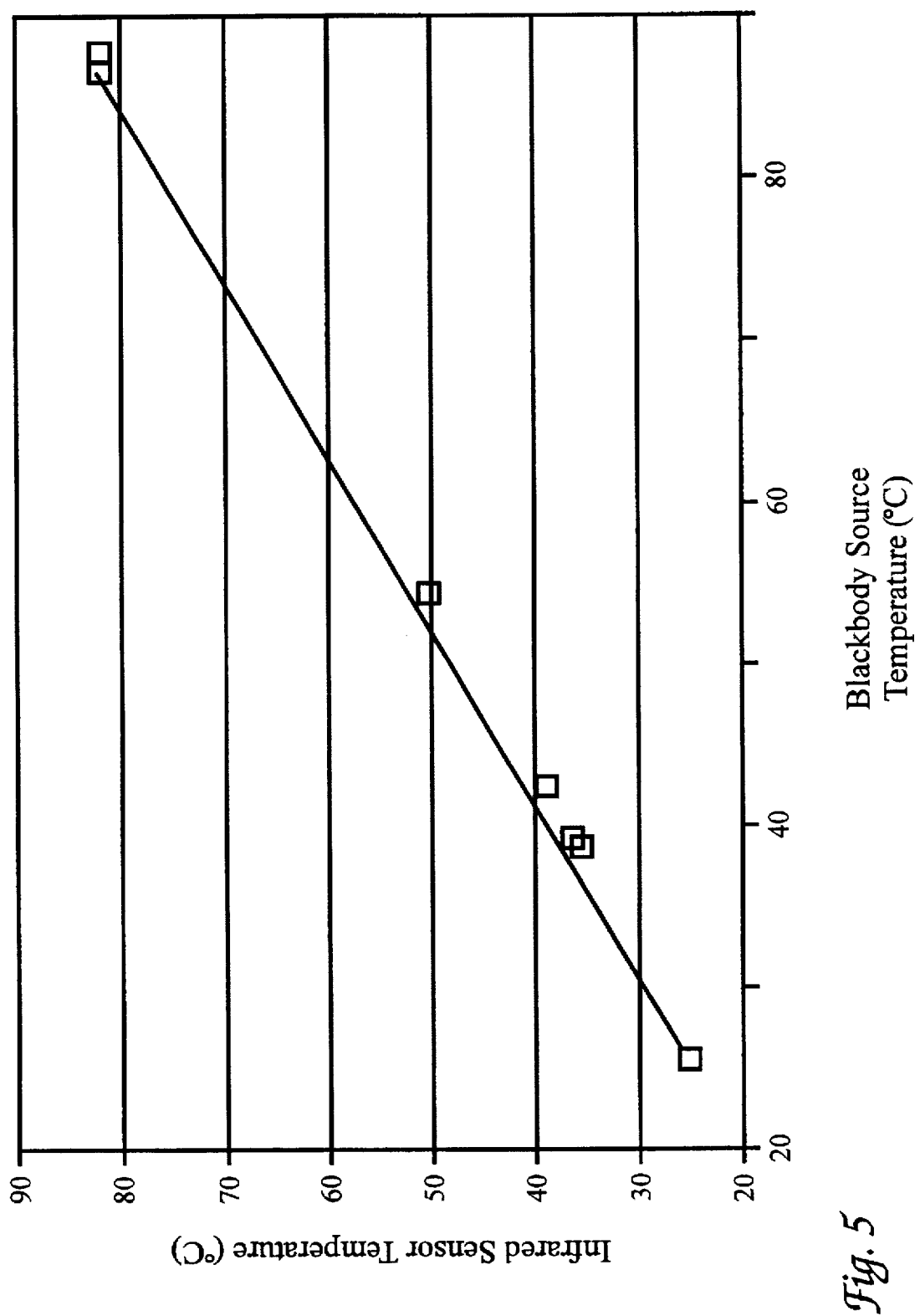
FIG. 5 shows a typical calibration chart for the thermal testing system of FIG. 1.

A calibration procedure is then used to calibrate the infrared sensor 90 using infrared radiation emitted by the emitter 70 of the blackbody source 65. A typical calibration procedure comprises (i) setting the blackbody source 65 to emit radiation at a temperature $T_b$, (ii) recording the temperature $T_c$ measured by the infra-red sensor when the sensor is focused on the blackbody source 65, and (iii) repeating steps (i) to step (ii) for different temperatures $T_b$, and plotting each $T_b$ against each $T_c$ to obtain a calibration curve for calibration of the infrared sensor 90. For example, a suitable calibration procedure comprises (i) setting the blackbody source 65 to emit radiation at room temperature (about 25° C.), and thereafter at 20° C. increments until a temperature of 200° C., (ii) at each 20° C. interval, recording the temperature reading of the readout 170 of the blackbody source 65, and the corresponding temperature reading of the infrared sensor 90, and (iii) plotting the two corresponding temperature readings against one another to obtain a calibration curve for the infrared sensor 90, as shown in FIG. 5. The calibration curve, or the slope of the calibration curve when the curve is substantially a straight line, can be used to determine accurate and correct temperatures of the infrared sensor 90 when the infrared sensor 90 is focused on the powered semiconductor device 20.

Preferably, the calibration curve is electronically determined using simultaneous output signals from the blackbody source 65 and infrared sensor 90. A conventional data logger 115 circuit can be used to monitor and record the output signals, and a conventional data analysis circuit can be used to determine the calibration curve from the signals of the blackbody source 65 and infrared sensor 90.

After calibration, the XYZ table 130 is readjusted so that the blackbody source 65 is removed from the field of view 87 of the sensor assembly 75, and the semiconductor device 20 re-positioned below the infrared sensor. It has been further discovered that adjusting the focus of the calibrated infrared sensor 90 by an amount F, sufficient to compensate for a thermal expansion movement of the electronic component 25 and package 30 caused by a rise in temperature of the electronic component 25 resulting from operation of the component by the power source, allows measurement of the junction temperature $T_j$ of the electronic component 25 to an accuracy of greater than 5%, and more typically from 2 to 3%, without removing the package 30 of the electronic component 25. Adjustment of the focus of the infrared sensor 90 is performed by adjusting the gimbal mechanism located between the sensor assembly 75 and the adjusting arm supporting the sensor assembly 75, so that the infrared sensor 90 is rotated by a small amount in a fixed plane perpendicular to the surface of the semiconductor device 20. Preferably, $F_c$ comprises a rotation of the infrared sensor 90 of about 1 to about 12 degrees, and more preferably from about 3 to about 8 degrees.

The data logger 115 processes the radiance measurement signals from the infrared system and directs the processed signals to a data analyzer 110 such as the computer system to analyze the signals. The data analyzer 110 ensures that the semiconductor device 20 is powered and operational, and calibrates the signals measured by the infrared sensor 90 using the calibration curve to provide the actual temperature readings measured by the infrared sensor 90. In this manner, the actual junction temperature values, or other thermal measurements, are made on the semiconductor device 20.

Optionally, immediately after the thermal measurements are made, the blackbody source 65 is re-positioned below the field of view 87 of the infrared sensor 90 and the calibration procedure is repeated. The second calibration curve is compared to the first calibration curve to ensure that the calibration of the infrared sensor 90 did not change during the measurement and data analysis procedure.

Many different thermal characteristics can be measured using the thermal testing apparatus and board of the present invention as apparent to one of ordinary skill in the art. Thus, the exemplary thermal properties and temperature measurements provided herein to illustrate use of the invention should not be used to limit the scope of the invention. Exemplary temperature measurement techniques include junction temperature, thermal resistance, package 30 and board temperatures, thermal dissipation, and thermal response time. Junction temperature $T_j$, is the temperature of the transition regions between different portions of the electronic component 25 that have asymmetrical electrical conductivities, such as for example p-type and n-type semiconductor portions, where most of the heat of the semiconductor device 20 is generated. Junction temperature is one of the primary factors affecting the reliability and performance of semiconductor devices 20. Package 30 or case temperature is the temperature of the package 30 in which the electronic component 25 is mounted and board temperature is the temperature of the printed circuit board on which the semiconductor device 20 is mounted. Thermal response time is the time required to reach 90% of the final value of a junction temperature caused by the application of a step function power dissipation when a reference temperature of the semiconductor device 20 is held constant. Power dissipation is the power dissipated in a single semiconductor junction or in a packaged semiconductor device 20. The heat flow or thermal dissipation of the semiconductor device 20, which is the rate at which heat flows from the electronic component 25 and out of the package 30, traditionally expressed in °C./Watt, can also be measured. Measuring the heat dissipation factor of the semiconductor device 20 within its package 30 facilitates manufacture of improved package 30 designs and materials.

Thermal resistance is the temperature difference from a junction of the electronic component 25 to some reference point $T_x$ such as ambient or package 30 temperature, divided by the power dissipation of the semiconductor device 20, and measures the ability of the semiconductor device 20, package 30 and circuit board environment to remove heat from the semiconductor device 20. The thermal resistance of a semiconductor device 20 is calculated from the package or ambient temperature $T_x$, the junction temperature $T_j$, and the power dissipation $P_d$ of the semiconductor device 20. Typically, a junction in the electronic component 25 having the highest power dissipation density is selected for measurement, and the packaged semiconductor device 20 is considered to achieve thermal equilibrium when the measured temperature difference, junction to package or ambient, reaches approximately 90 to 99% of its final value. The temperature difference at that time would change to a rate less than:

$$\frac{d(T_j - T_x)}{dt} \geq 0.03 \frac{(T_j - T_x)}{t}$$

where T is time after application of a power dissipation increment. The total time required for stabilization is typically less than 25 minutes. Alternatively, the thermal resistance can be calculated knowing the peak junction temperature $(T_{j(PEAK)})$ and the average junction temperature $(T_{j(AVG)})$. The thermal resistance is $R_{\theta jc(PEAK)} = T_{j(PEAK)} - T_x + P_d$. Where $P_d$ in Watts, is a power dissipated in a single semiconductor device 20 including the package 30 of the device.

The thermal testing apparatus can also be used to provide multiple junction temperatures of a device 20, such as a multichip device, rather than a single junction temperature to yield a temperature distribution within the device 20. A temperature distribution is particularly useful for hybrid and large die integrated circuits because substantial temperature variations can exist within such devices. When measuring the temperature distribution, between 5 to 25 individual junctions are simultaneously monitored to allow measuring of hot spots in the device 20. Mapping of the thermal distribution of the electronic component 25 is also particularly useful as the size of the junctions in the device decrease and as the packing density of the electronic components 25 increase.

Several different spacial temperature distributions can be imaged. For example, a computer program can be used to create a frequency distribution of the temperature within an area of interest, commonly known as a histogram. A temperature profile that graphically displays the temperature distribution across a single line of points across the semiconductor device 20 can also be generated, and this image compared against temperature profiles of different integrated circuit chips for quality assurance and thermal design optimization purposes. Furthermore, the infrared sensor 90 can also be zoomed in a particular area to magnify the thermal image of the area. Isotherms and thermal contours that highlight areas with equal radiance or temperature can also be used to identify given temperature levels within an image.

Although the present invention has been described in considerable detail with regard to the preferred versions thereof, other versions are possible. For example, the alternative sensors can also be used. Therefore, the appended claims should not be limited to the descriptions of the preferred versions contained herein.

What is claimed is:

1. A method for measuring a junction temperature $T_j$ of an electronic component encapsulated in a package, without removing the package, and during operation of the electronic component by a power supply, the method comprising the steps of:

(a) positioning the electronic component in a field of view of an infrared sensor, during operation of the electronic component by the power supply;

(b) focusing the infrared sensor on the electronic component inside the package to obtain (i) a sharp outline of the electronic component, and (ii) a maximum temperature reading;

(c) removing the electronic component from the field of view of the sensor;

(d) positioning a blackbody source capable of emitting infrared radiation at different wavelengths at substantially the same focal point as the infrared sensor;

(e) calibrating the infrared sensor using the blackbody source;

(f) replacing the blackbody source with the electronic component while continuing to operate the electronic component by the power supply;

(g) adjusting the focus of the calibrated infrared sensor by an amount $F_c$ sufficient to compensate for a thermal expansion movement of the electronic component and package caused by a rise in temperature of the electronic component resulting from operation of the component by the power supply; and (h) measuring the junction temperature $T_j$ of the electronic component to an accuracy of better than 5% without removing the package of the electronic component.

2. The method of claim 1, wherein the junction temperature $T_j$ of the electronic component is measured to an accuracy of better than 2%.

3. The method of claim 1, wherein the junction temperature $T_j$ of the electronic component is measured to an accuracy of at least about 1° C. at a temperature of about 50° C.

4. The method of claim 1, wherein the step of calibrating the infrared sensor comprises the step of deriving a calibration curve for the infrared sensor by the steps of:

(i) setting the blackbody source to emit radiation at a temperature $T_b$, (ii) recording the temperature $T_c$ measured by the infrared sensor when the sensor is focused on the blackbody source, (iii) repeating steps (i) to step (ii) for different temperatures $T_b$, and plotting each $T_b$ against each $T_c$ to obtain a calibration curve for calibration of the infrared sensor.

5. The method of claim 1, further comprising the step of using the measured junction temperature $T_j$ of the electronic component to determine a thermal characteristic of the electronic component and package selected from the group consisting of thermal resistance, power dissipation factor, and thermal response time.

6. The method of claim 1, wherein the junction temperature $T_j$ is the temperature of at least one transition region between portions of the electronic component having different electrical properties.

7. The method of claim 1, wherein the package of the electronic component comprises an electrically insulative packaging material.

8. The method of claim 1, wherein the electronic component in the package is a component selected from the group consisting of an integrated circuit chip, resistor, transistor, capacitor, induction coil, and switching devices.

9. The method of claim 1, comprising the initial steps of:

(i) selecting an optical sensor having a field of view substantially aligned with the field of view of the infrared sensor;

(ii) positioning the electronic component in the field of view of the optical sensor, during operation of the electronic component by the power supply; and (iii) focusing the optical sensor on the package of the electronic component to obtain a image of the package to facilitate focusing of the infrared sensor.

10. A method for measuring a junction temperature $T_j$ of an electronic component in a package, without removing the package, and during operation of the electronic component by a power supply, the method comprising the steps of:

(a) selecting a sensor assembly having a field of view, the sensor assembly comprising (i) an optical sensor, and (ii) an infrared sensor;

(b) positioning the electronic component in the field of view of the sensor assembly, during operation of the electronic component by the power supply;

(c) coarse focusing the optical sensor of the sensor assembly on the package of the electronic component to obtain an image of the package;

(d) fine focusing the infrared sensor on the electronic component inside the package to obtain (i) a sharp outline of the electronic component, and (ii) a maximum temperature reading;

(e) removing the electronic component from the field of view of the sensor;

(f) deriving a calibration curve for the infrared sensor by the steps of:

(1) positioning a blackbody source capable of emitting infrared radiation at a temperature $T_b$ in the field of view of the infrared sensor;

(2) recording the temperature $T_c$ measured by the infrared sensor when the sensor is focused on the blackbody source;

(3) repeating steps (1) to (2) for different temperatures $T_b$, and plotting each $T_b$ against each $T_c$ to obtain a calibration curve for calibration of the infrared sensor;

(g) replacing the blackbody source with the electronic component while continuing to operate the electronic component by the power supply;

(h) adjusting the focus of the infrared sensor by an amount $F_c$ sufficient to compensate for a thermal expansion movement of the electronic component and package caused by a rise in temperature of the electronic component resulting from operation of the component by the power supply; and (i) measuring the junction temperature $T_j$ of the electronic component, wherein the temperature $T_j$ is measured to an accuracy of better than 5% without removing the package of the electronic component.

11. The method of claim 10, further comprising the step of verifying calibration of the infrared sensor after step (i).

12. An apparatus for measuring a junction temperature of an electronic component in a package, without removing the package, and during operation of the electronic component, the apparatus comprising:

(a) a sensor assembly having a field of view, the sensor assembly comprising an infrared sensor;

(b) an adjustable platform in the field of view of the sensor assembly;

(c) a blackbody source mounted on the platform, the blackbody source having a emitter capable of emitting infrared radiation at different temperatures $T_b$ for calibration of the infrared sensor; and (d) a holder mounted on the platform for holding the package with the electronic component therein, wherein the blackbody source and holder are mounted on the platform so that the package of the electronic component when held in the holder is substantially in the same focal plane as the emitter of the blackbody source.

13. The apparatus of claim 12, further comprising means for determining a calibration curve for the infrared sensor using the blackbody source.

14. The apparatus of claim 13, wherein the means for determining a calibration curve for the infrared sensor comprises:

(i) means for setting the emitter of the blackbody source to emit radiation at different temperatures $T_b$;

(ii) a recorder for recording the temperatures $T_c$ measured by the infrared sensor for each of the temperatures $T_b$, when the infrared sensor is focused on the blackbody source; and (iii) means for generating a calibration curve for the infrared sensor by plotting each $T_b$ temperature against the corresponding $T_c$ temperature.

15. The apparatus of claim 12, further comprising means for adjusting a focus of the infrared sensor by an amount $F_c$ sufficient to compensate for thermal expansion movement of the electronic component and package caused by a rise in temperature of the electronic component resulting from operation of the component.

16. The apparatus of claim 15, wherein the means for adjusting the focus of the infrared sensor comprises an adjustable gimbal mechanism that allows rotation of the infrared sensor in a fixed plane.

17. The apparatus of claim 12, further comprising a positioning mechanism assembly for moving the platform so that the blackbody source or holder can be positioned in the field of view of the sensor assembly.

* * * * *